(12) United States Patent  
Ziv et al.

(10) Patent No.: US 6,569,117 B1  
(45) Date of Patent: May 27, 2003

(54) BLOOD SAMPLING/INJECTING VALVE

(75) Inventors: David Ziv, Kibbutz Baram (IL); Tomer Gil, Kibbutz Yiron (IL); Freddy Zinger, Raanana (IL)

(73) Assignee: Elcam+Plastic Cooperative Agriculture Association Ltd., Kibbutz Baram (IL)

( * ) Notice: Subject to any disclaimer, the term of this patent is extended or adjusted under 35 U.S.C. 154(b) by 0 days.

(21) Appl. No.: 09/868,850

(22) PCT Filed: Dec. 13, 1999

(86) PCT No.: PCT/IL99/00678

§ 371 (c)(1),  
(2), (4) Date: Jul. 26, 2001

(87) PCT Pub. No.: WO00/40291

PCT Pub. Date: Jul. 13, 2000

(30) Foreign Application Priority Data

Jan. 1, 1999 (IL) .................................................. 127900

(51) Int. Cl.⁷ .............................................. A61M 5/178
(52) U.S. Cl. ............................ 604/164.01; 604/167.01; 604/181; 604/246; 604/256
(58) Field of Search ..................... 604/93.01, 164.01, 604/164.12, 166.01, 167.01–167.06, 168.01, 181, 246, 248, 249, 256

(56) References Cited

U.S. PATENT DOCUMENTS

| | | | | |
|---|---|---|---|---|
| 3,965,910 A | * | 6/1976 | Fischer | 604/249 |
| 3,996,923 A | * | 12/1976 | Guerra | 600/579 |
| 4,131,127 A | * | 12/1978 | Ferro et al. | 137/315.07 |
| 4,301,811 A | * | 11/1981 | Layton | 600/487 |
| 4,450,854 A | * | 5/1984 | Alexander et al. | 137/246.12 |
| 4,506,691 A | * | 3/1985 | Tseo | 137/1 |
| 4,819,684 A | | 4/1989 | Zaugg et al. | |
| 5,147,333 A | | 9/1992 | Raines | |
| 5,393,035 A | * | 2/1995 | Steele | 137/556.6 |
| 5,636,975 A | * | 6/1997 | Tiffany et al. | 137/454.4 |

FOREIGN PATENT DOCUMENTS

| | | | | |
|---|---|---|---|---|
| DE | 31 42 524 A1 | * | 5/1983 | A61M/5/31 |
| EP | A1 0 240 590 | | 10/1987 | |
| WO | WO 95/00188 | | 1/1995 | |

* cited by examiner

*Primary Examiner*—Henry Bennett  
*Assistant Examiner*—Andrea M. Ragonese  
(74) *Attorney, Agent, or Firm*—Oliff & Berridge, PLC

(57) ABSTRACT

A blood sampling/injecting valve includes a housing formed with a cavity extending along a longitudinal axis of the housing, the cavity is adapted for sealingly receiving a syringe Luer connector and the housing further is provided with an inlet port and an outlet port. The valve includes also a plunger formed with a through going communication conduit and with a flow path for a liquid. The flow path is configured as a recess, which is opened to a top face of the plunger and to a lateral surface of the plunger. The plunger is axially displaceable by the Luer connector between a flow position in which the communication conduit directly communicates between the inlet port and the outlet port and a sampling/injecting position in which the flow path directly communicates between the Luer connector and the outlet port, while the inlet port is disconnected from the outlet port. The plunger is normally biased into the flow position. The flow path and the top face of the plunger are easily accessible for swabbing and the flow path is configured in such a manner, that the liquid flowing through the flow path is prevent from accumulating thereinto.

17 Claims, 5 Drawing Sheets

BLOOD SAMPLING/INJECTING VALVE

BACKGROUND OF THE INVENTION

1. Field of Invention

The present invention is in the field of medical valves and in particular it is concerned with a valve suitable for drawing blood samples from an individual or for injecting to an individual through an infusion tubing system.

2. Description of Related Art

A variety of infusion tubing systems are known for various treatments requiring liquid administration to a patient. However, at times it is required to draw a blood sample through the same infusion line or to inject through the same line some treatment liquid. Such procedures are heretofore carried out by using different three-way stop cock valves and other shut-off valves.

Typically, it is a requirement to draw "fresh" blood samples, i.e. blood which has not been mixed with other agents, or which has not been standing for a while in a tubing section which may thus result in obtaining false indications.

It is another growing requirement that blood sampling and injecting devices, in particular those components which are exposed to the environment, be easily approachable for wiping with a disinfectant swab. Such an operation is often referred to in the art as "swabbing", and, respectively swab approachable zones are referred to as "swabbable".

U.S. Pat. No. 4,819,684 discloses an injection shut-off valve comprising a housing with connections for inlet end outlet lines. The housing includes an orifice for introducing an.injection syringe and a valve installed within the housing including a deformable diaphragm. In a non-injection state, the valve device seals off fluid flow between the inlet lines and the outlet lines on the one hand, and the orifice on the other hand. However, during injection, the diaphragm is deformed to create an opening such that fluid flow from the inlet to the housing is shut off. During the formation of the diaphragm the orifice is brought into fluid connection with the outlet line from the housing, thus making it possible for injecting fluid to pass through the housing into the outlet line and to the patient.

However, by some of the embodiments of the '684 patent portions of the valve which come into contact with the syringe are not swabable, whereas in other embodiments the device is suitable only for injecting liquid therethrough, while drawing a blood sample is not possible, as the device operates as a one-way valve.

It is an object of the present invention to provide a novel sampling/injecting valve in which the above referred to disadvantages are significantly reduced or overcome, and wherein the above desiderata are fulfilled.

SUMMARY OF THE INVENTION

It is an object of the present invention to provide a novel sampling/injecting valve suitable for operating with an infusion line whereby activating of the valve is carried out by a luer-type connecting member, typically of a syringe, whereby a blood sample may be drawn from a patient or a liquid may be injected to the patient.

In accordance with the present invention, there is provided a blood sampling/injecting valve comprising:

a housing formed with a cavity extending along a longitudinal axis of the housing, said cavity having an opening adapted for sealingly receiving a syringe Luer connector; said housing further comprising an inlet port and an outlet port;

a plunger formed with a communication conduit and a flow path formed at a top face of the plunger facing the opening of the housing; said plunger being axially displaceable by the Luer connector between a flow position in which the conduit communicates between the inlet and the outlet port and a sampling/injecting position in which the flow path is in flow communication with the outlet port, while the outlet port is disconnected from the inlet port; said plunger being normally biased into said flow position. By one example, the communication conduit is an annular, peripheral groove formed at the plunger.

By one embodiment, the communication conduit is a bore transversely extending through the plunger, in which case the plunger is rotatably restrained within the cavity.

In accordance with a most preferred embodiment of the present invention, the entire space of the flow path is swabable, i.e. a disinfectant swab may be easily introduced into the flow path for disinfecting thereof.

In accordance with one design of the invention, the inlet port and the outlet port transversely extend with respect to said longitudinal axis. In accordance with one arrangement, the outlet port and the inlet port may be co-axial with one another.

By one specific embodiment, the plunger is retained within the housing by a snap-type arrangement, wherein the plunger is introduced into the cavity of the housing via the opening, overcoming a radially projecting retainer portion, typically annular.

In accordance with another specific design, the plunger is biased into the flow position by a springy portion integrally extending from a bottom face thereof bearing a bottom wall of the housing.

In order to obtain improved sealing in the flow position, the plunger and the cavity of the housing has corresponding tapering cross-sections. In accordance with such an arrangement, the housing is formed with a removable bottom cap for insertion of the plunger during assembly thereof. The cap may be fixedly or removably attached to the housing.

In order to ensure that the plunger does not rotate within the housing, so as to obtain alignment of the communication conduit with the inlet and outlet ports, the plunger is formed, at least at the lower part thereof, with a portion having a non-circular cross-section received within a portion of the cavity, having a corresponding cross-section.

In order to increase sealing of the valve, at least in its flow-position, a sealing arrangement.is provided between the plunger and the walls of the cavity, at least at a location above the communication conduit, when the plunger is in the flow position. In accordance with such an arrangement, the plunger and the walls of the cavity are integrally formed with sealing rings and sealing grooves, respectively, engaging one another in the flow position.

By one embodiment of the invention, the flow path is a recessed well, formed at the top face of the plunger, and having an open wall portion at a side facing the outlet port, whereby at the sampling injecting position, the open wall portion is in flow communication with the outlet port of the housing.

In accordance with another embodiment of the invention, the flow path comprises one or more spacers, ensuring a clearance between a fore end of the luer connector of a syringe and the top face of the plunger, the arrangement being such that at the sampling-injecting position, said top face is in flow communication with the outlet port.

An important character of the valve in accordance with the present invention is lack of so-called dead-space, i.e. a volume in which blood or injected liquid may accumulate between sampling or injecting procedures, which may be either hazardous for a patient, or lead to false indications in case of blood sampling.

BRIEF DESCRIPTION OF THE DRAWINGS

For better understanding, the invention will now be described by way of reference to some non-limiting embodiments, by way of reference to the accompanying drawings, in which.

DETAILED DESCRIPTION OF PREFERRED EMBODIMENTS

Figure 1:
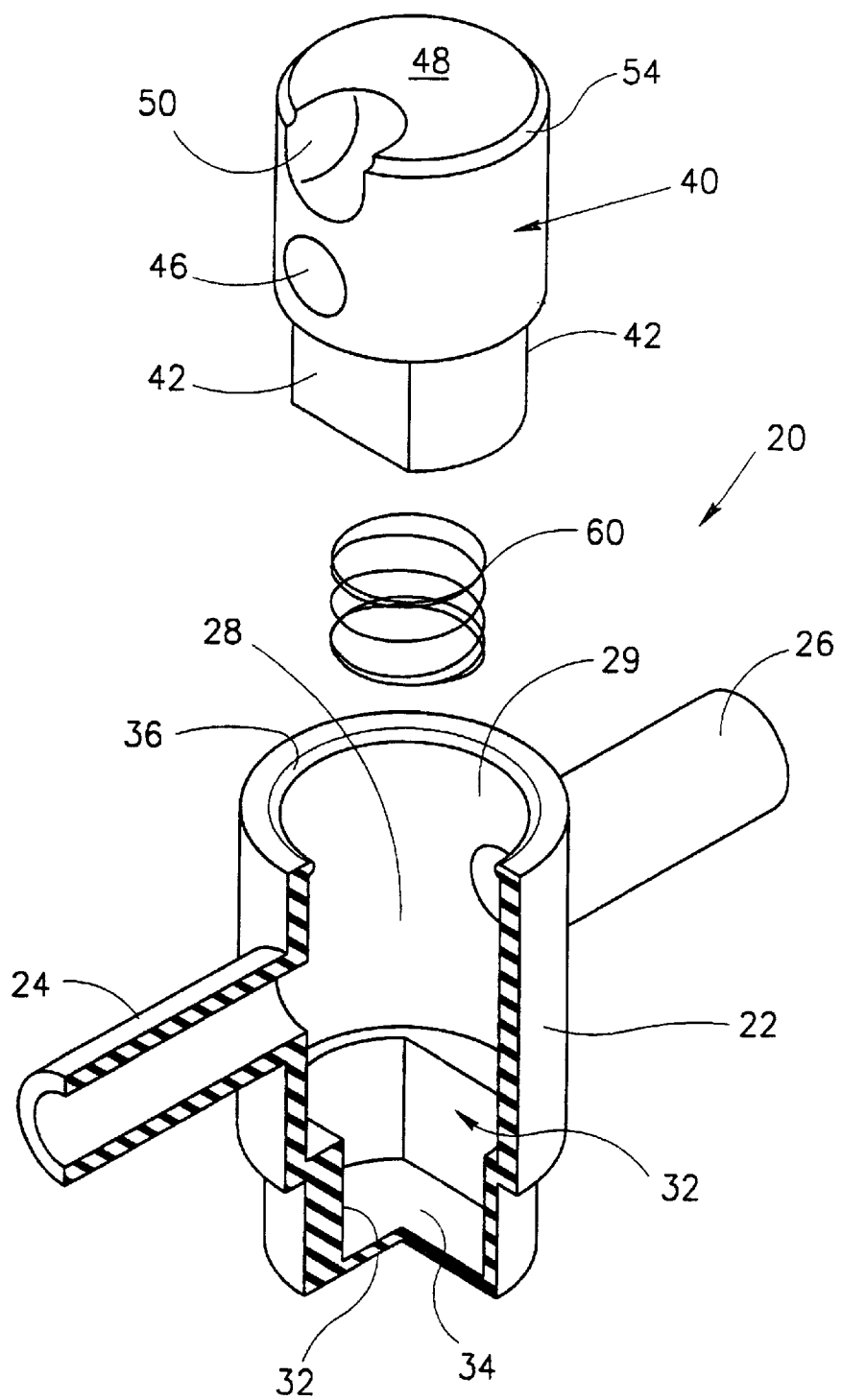
FIG. 1 is an exploded perspective view of the valve in accordance with a first embodiment of the present invention.

In FIGS. 1 and 2 there is seen a valve generally designated 20, the valve comprising an essentially cylindrical housing 22 fitted with an outlet port 24 and a co-axial inlet port 26, which in the present example are transverse to a longitudinal axis of a central cavity 28 formed in the housing having a top opening 29. Typically, inlet port 26 is connected by suitable tubing to an infusion set and outlet port 24 is connected via suitable tubing to a patient.

Cavity 28 is formed at a bottom end thereof with two straight wall portions 32 extending to a base wall 34 of housing 22.

Cavity 28 is formed at its top end with an annular rim 36 for the purpose to become apparent hereinafter.

A plunger generally designated 40 is essentially cylindrical and is adapted for snugly fitting within the cavity 28 of housing 22. Plunger 40 comprises at its bottom end a portion formed with two straight walls 42 which in the assembled positions of FIGS. 2A or 2B prevent rotation of the plunger 40 within the cavity 28 of housing 22.

Plunger 40 is formed with a throughgoing bore 46 and a top surface 48 is formed with a well-like recess constituting a flow path 50 having an opening at the top surface 48 and also at a side wall of the plunger 40 which in the assembled position of FIGS. 2 faces the inlet port 26. Plunger 40 is formed at its top face with annular recess 54 corresponding with the dimensions of annular rim 36 of housing 22.

Figure 2A:
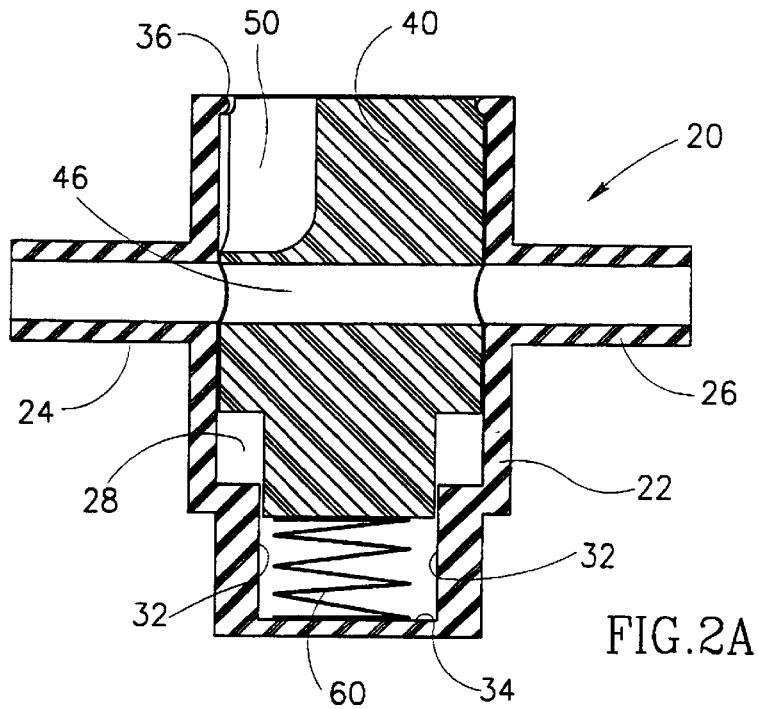
FIG. 2A is a cross-sectional view of the valve seen in FIG. 1 in the flow position.

Coil spring 60 is provided for biasing the plunger 40 into an upward position as seen in FIG. 2A.

For assembling the valve, spring 60 is introduced into the cavity 28 of housing 22 and then the plunger 40 is forcefully introduced through the opening 29 of cavity 28 overcoming the resistance of rim 36. In the assembled position, recess 54 of plunger 40 is biased against rim 36, retaining the plunger within the housing.

Further attention is now directed to FIG. 2A in which the valve 20 is shown in a so-called flow position, wherein bore 46 is in alignment with outlet port 24 and inlet port 26, whereby fluid flow between these ports is enabled, e.g. between an infusion source and a patient. However, fluid flow between either outlet port 24 or inlet port 26 and between the flow path 50, is interdicted.

Figure 2B:
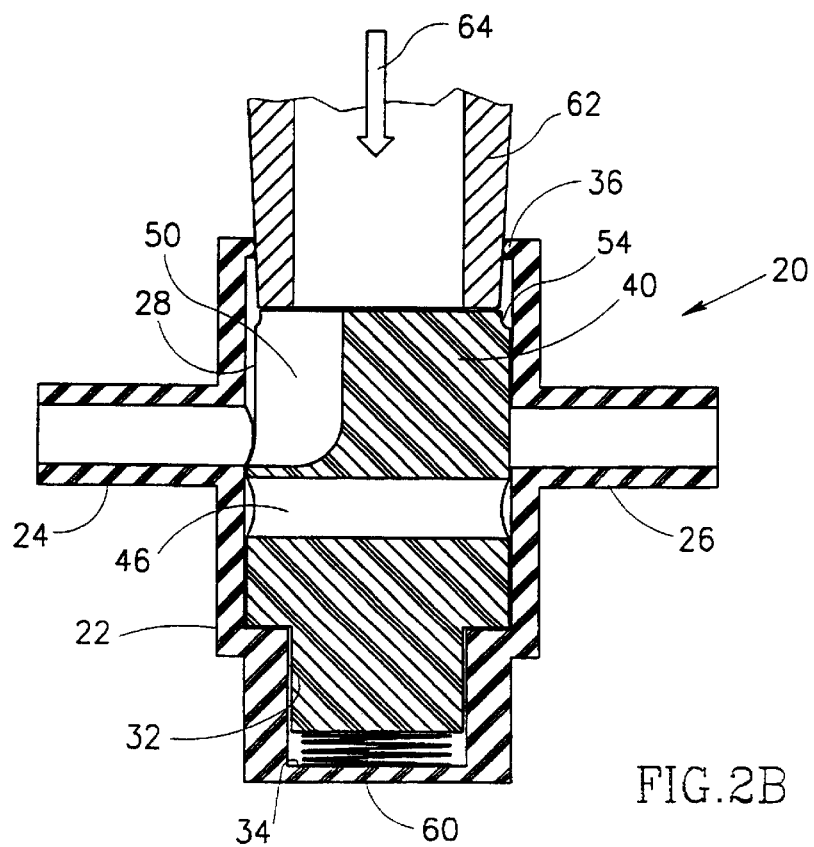
FIG. 2B is a cross-sectional view of the valve seen in FIG. 1 in the sampling/injecting position.

Further attention is now directed to FIG. 2B, wherein a section of luer-type connection 62, typically being the end of a syringe. Upon applying force in direction of arrow 64, the plunger 40 is displaced into the position shown in FIG. 2B, wherein the bore 46 disengages from the outlet and inlet ports 24 and 26 respectively, disconnecting flow communication therebetween. Simultaneously, flow path 50 engages the outlet port 24 wherein it is now possible to draw a blood sample or inject a liquid through the outlet port 24. As can be appreciated, in this position there is now flow between inlet port 26 and flow path 50.

The arrangement is such that upon withdrawal of Luer connector 62, plunger 40 is spontaneously biased into the flow position of FIG. 2A, wherein flow between the inlet port and the outlet port is resumed.

Typically, after such a procedure, disinfecting is required and for that purpose the flow path 50 is of significant size and is configured to provide good access for introducing a disinfecting swab.

Figure 3:
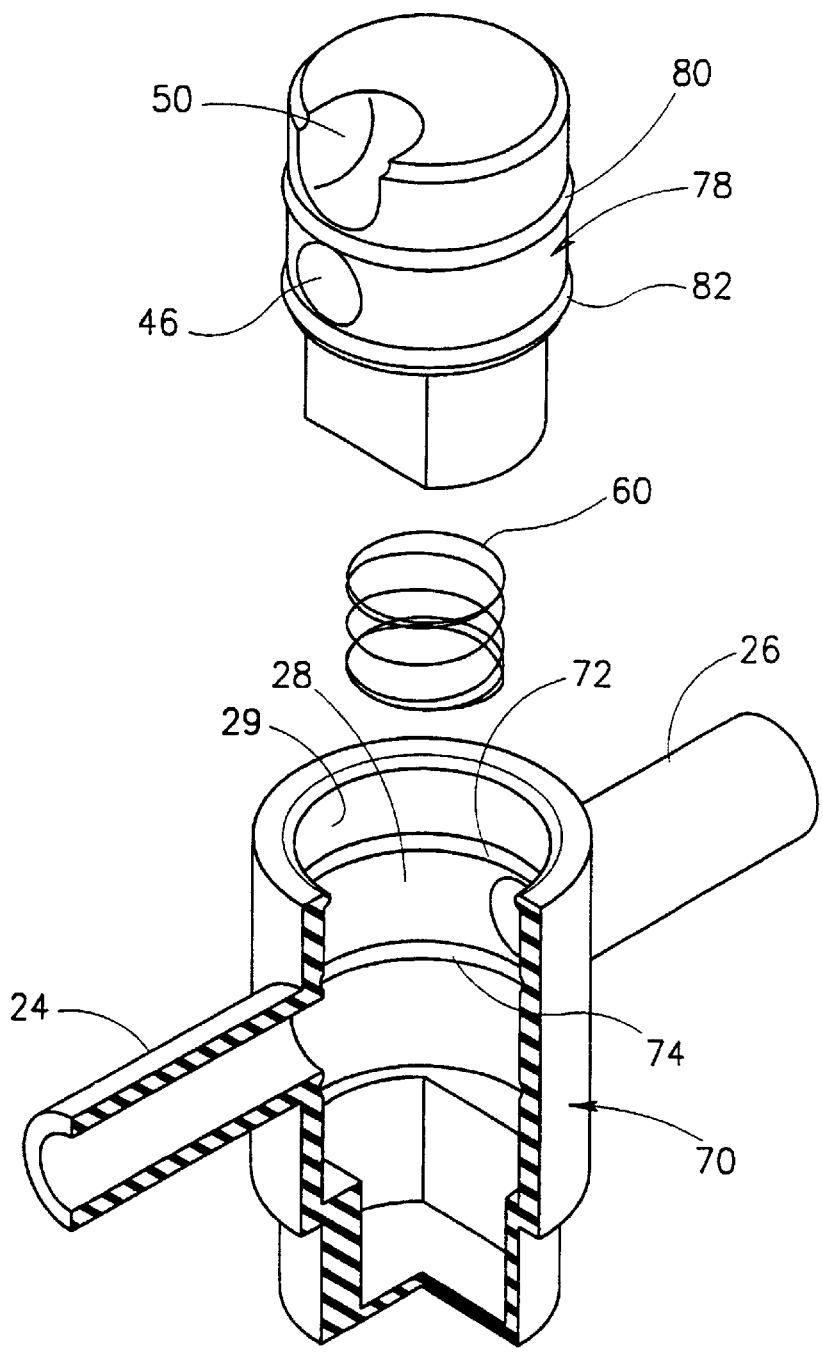
FIG. 3 is an exploded perspective view of a valve similar to the valve of FIG. 1, fitted with sealing means.

Further attention is now directed to FIG. 3 which is essentially similar to the embodiment of FIGS. 1 and 2, and accordingly identical elements were given the same reference numbers, for the sake of clarity.

In accordance with this embodiment, the housing 70 is formed with two annular recesses 72 and 74, one above and one below outlet and inlet ports 24 and 26, respectively. Plunger 78 is formed with two annular rings 80 and 82, which in the flow position of this embodiment (not shown) are adapted for sealing engagement within the corresponding recesses 72 and 74, thus preventing leakage of fluid through opening 29 of cavity 28. Rings 80 and 82 may be O-rings made of resilient material fitted within suitable recesses formed on the plunger 78 or, alternatively, the entire plunger may be made of a somewhat resilient material allowing sealing engagement of the rings 80 and 82 with the corresponding recesses 72 and 74.

Figure 4:
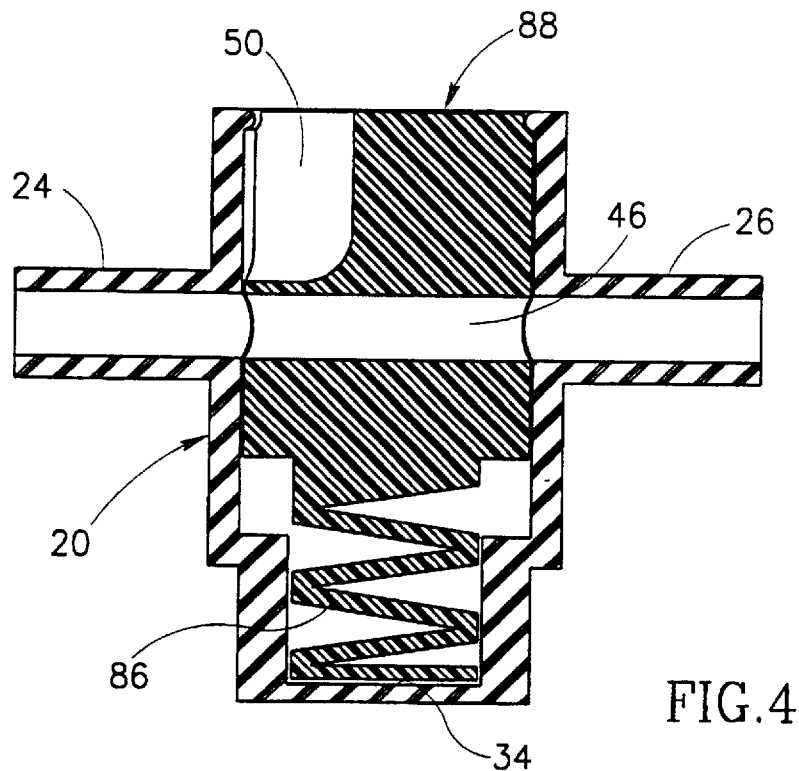
FIG. 4 is a cross-sectional view of a valve in accordance with the present invention, wherein biasing means are integral with the plunger.

The embodiment of FIG. 4 is essentially similar to the embodiment of FIGS. 1 and 2 and here again the same reference numbers were used for identical elements. The embodiment of FIG. 4 differs in that the spring element 86 is integrally formed with the plunger 88 and is adapted for biasing against the bottom wall 34 of housing 22 so as to bias plunger 88 into the flow position seen in FIG. 4. This arrangement is somewhat cheaper in manufacture and assembly than the embodiment of FIGS. 1 and 2, and is more commercial, in particular for disposable medical equipment.

Figure 5:
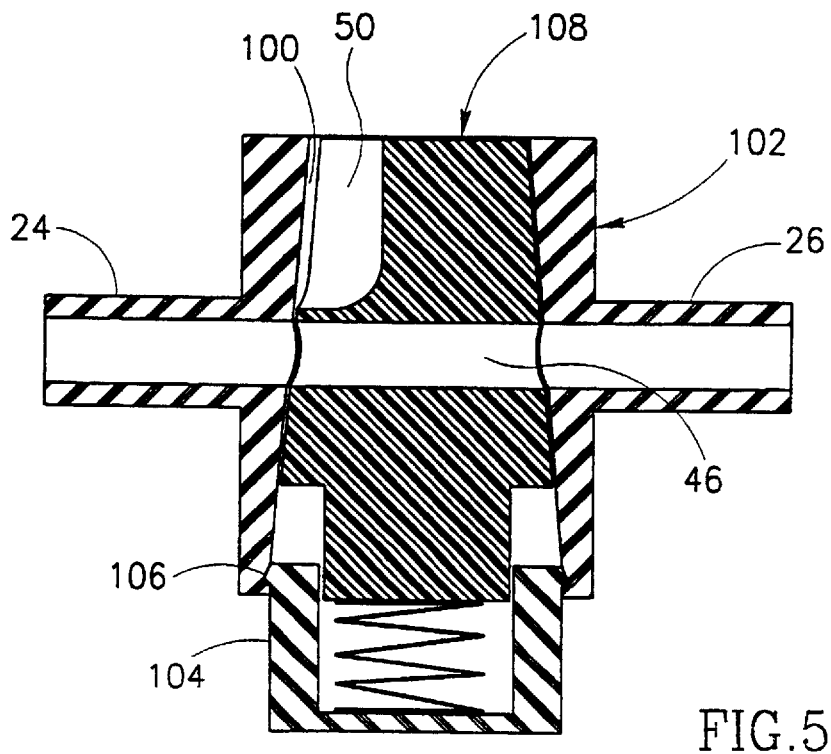
FIG. 5 is a cross-sectional view of another embodiment of the valve in accordance with the present invention.

In the embodiment of FIG. 5 the cavity 100 of housing 102 has a tapering cross-section and a cap-like base member 104 attachable to the housing 102, for example, by a snap-type engagement 106. Plunger 108 has a tapering cross-section as well, corresponding with cross-section of cavity 100, whereby in the flow position seen in this Figure, plunger 108 is snugly received within the cavity 100 with the connecting the bore 46 being aligned with outlet port 24 and inlet port 26. The tapering arrangement of FIG. 5 provides a fluid-tight sealing between the housing 102 and plunger 108 in the flow position.

However, it will be noted that in accordance with the embodiment of FIG. 5 the plunger 108 is introduced from the bottom neck of the housing 102 prior to attaching base member 104.

As can readily be understood, the embodiments of FIGS. 3–5 operate in a similar manner as explained with reference to FIGS. 1 and 2, wherein the well-shaped flow path 50 is formed in a position facing the outlet 24, wherein at the flow position it is not in flow communication with the outlet port 24, and in the sampling/engaging position it engages with outlet port 24, while the flow communication through bore 46 between outlet port 24 and inlet port 26 is prevented.

Figure 6A:
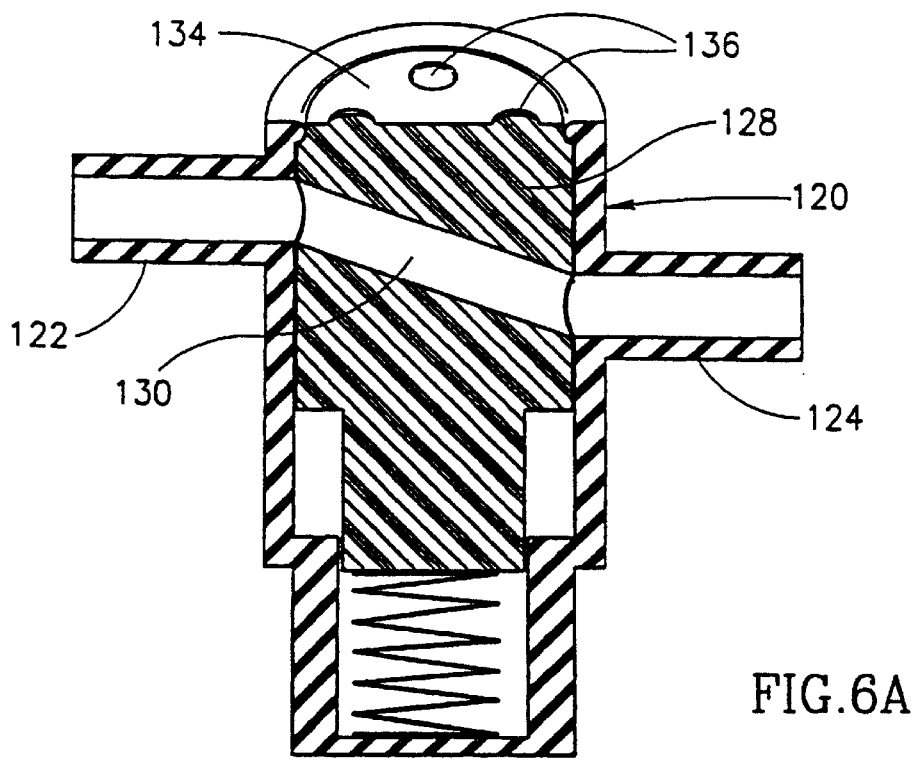
FIG. 6A is a perspective cross-sectional view in accordance with still another embodiment of the present invention shown in the flow position.
Figure 6B:
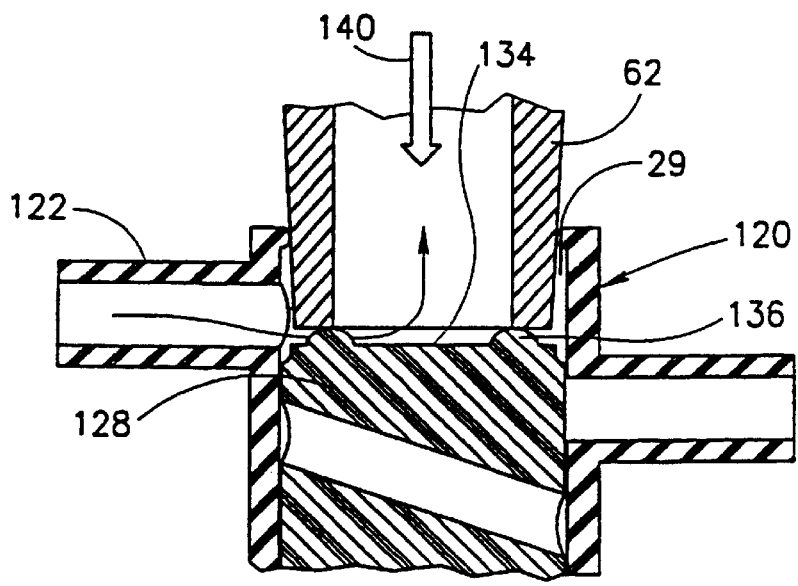
FIG. 6B is a cross-sectional view of the valve seen in FIG. 6a in the sampling/injecting position.

Further attention is now directed to FIGS. 6A and 6B illustrating still another embodiment of the valve of the present invention. In accordance with this embodiment, the housing 120 has a similar construction as that of housing 22 in FIG. 1, the exception being that the outlet port 122 and inlet port 124 are not aligned with one another. In a corresponding manner, the plunger 128 has a communication conduit 130 which extends at a suitable angle such that at the flow position seen in FIG. 6a it communicates between the outlet port 122 and inlet port 124.

In this embodiment the top face 134 of plunger 128 is formed with a plurality of bulges 136, defining a space constituting the flow path. This arrangement provides good access for applying a disinfecting swab to the flow path.

Upon introducing a Luer connector 62 (e.g. of a syringe) into the cavity of housing 120, its forehead engages bulges 136 and applying force in direction of arrow 140 displaces the plunger 128 into the sampling/injecting position seen in FIG. 6b, wherein liquid flow may be established between outlet port 122 and Luer connector 62 for sampling or injecting, as may be the case.

It is appreciated that in accordance with the embodiment of FIGS. 6, the plunger 128 is also biased into the flow position, as in the previous embodiments, and that suitable means are provided for preventing rotation of the plunger within the housing and for disengagement of the plunger therefrom.

It will further be noted that the opening 29 of the cavities 28 or 100 in either of the embodiments of the present invention is so dimensioned so as to sealingly engage with the Luer connector 62 to facilitate blood sampling drawing or injecting therethrough, i.e. to ensure tight vacuum required for drawing and to prevent leakage of liquids therethrough.

It can be easily appreciated that the configuration of the flow path in the above embodiments ensures easy flow of liquid therethrough without retaining in the flow path when the plunger is in the sampling/injection position.

It should be noted that in the embodiments of FIGS. 1–5 the flow path in the form of well-shaped recess as well as the flow path in the embodiment of FIG. 6 defined by the bulges 136 is entirely and conveniently swabable, i.e. allow easy access for disinfecting by a swab.

While preferred embodiments have been shown and described, it is to be understood that it is not intended thereby to limit the disclosure, but rather it is intended to cover all embodiments, modifications and arrangements falling within the spirit and the scope of the present invention as defined in the appended claims, mutatis mutandis.

What is claimed is:

1. A blood sampling/injecting valve, comprising:
   a housing formed with a cavity extending along a longitudinal axis of the housing, said cavity having an opening, said cavity is adapted for sealingly receiving a syringe Luer connector; said housing further comprising an inlet port and an outlet port;
   a plunger formed with a through going communication conduit and with a flow path, said flow path being configured as a recessed well formed in the plunger, said well being defined by an upper portion opened to a top face of the plunger and to a lateral surface of the plunger and faces an inwardly facing surface of the cavity; said plunger being axially displaceable by the Luer connector between a flow position in which the communication conduit directly communicates between the inlet port and the outlet port and a sampling/injecting position in which the flow path directly communicates between the Luer connector and the outlet port, while the inlet port is disconnected from the outlet port; said plunger being normally biased into said flow position; where the flow path and the top face of the plunger are easily accessible for swabbing and where the flow path is configured in such a manner, that liquid flowing therethough is prevented from accumulating thereinto.

2. A blood sampling/injecting valve according to claim 1, wherein the plunger is rotatably restrained within the cavity and wherein said communication conduit comprises a bore laterally extending through the plunger.

3. A blood sampling/injecting valve according to claim 1, wherein the plunger is provided with an annular groove formed adjacent the top face of the plunger.

4. A blood sampling/injecting valve according to claim 2, wherein the inlet port and the outlet port transversally extend with respect to said longitudinal axis.

5. A blood sampling/injecting valve according to claim 2, wherein the inlet port and the outlet port are coaxial.

6. A blood sampling/injecting valve according to claim 1, wherein the plunger is retained within the housing by a peripheral retainer rim formed at the opening of the housing.

7. A blood sampling/injecting valve according to claim 1, wherein the plunger is biased into the flow position by a springy portion integrally extending from a bottom face thereof, said springy portion bearing against a bottom wall of the housing.

8. A blood sampling/injecting valve according to claim 1, wherein the plunger and the cavity of the housing have corresponding tapering cross-sections.

9. A blood sampling/injecting valve according to claim 8, wherein the housing is formed with a removable base member.

10. A blood sampling/injecting valve according to claim 2, wherein the plunger is formed at least at a lower part thereof with a portion having a non-circular cross-section received within a portion of the cavity having a corresponding cross-section.

11. A blood sampling/injecting valve according to claim 1, wherein a sealing arrangement is provided between the plunger and the inwardly facing surface of the cavity at least at a location above the communication conduit, when the plunger is at the flow position.

12. A blood sampling/injecting valve according to claim 11, wherein the plunger and the inwardly facing surface of the cavity are integrally formed with sealing rings and sealing grooves, respectively.

13. A blood sampling/injecting valve according to claim 6, wherein the plunger and the cavity are dimensioned in such a manner, that at the flow position, the top face of the plunger is essentially flush with an edge of the opening of the cavity.

14. A blood sampling/injecting valve according to claim 1, wherein said well being further defined by a lower portion, opened to the lateral surface of the plunger, wherein said well is located in the plunger in such a manner, that when the plunger is brought into the sampling/injection position the upper portion thereof is in flow communication with the Luer connector and the lower portion thereof is in flow communication with the inlet port of the housing.

15. A blood sampling/injecting valve according to claim 1, wherein said inlet port is not coaxial to the outlet port, said communication conduit is not transversal with respect to the longitudinal axis and the flow path is formed with projections, arranged immediately on the top surface of the plunger, said spacing elements ensuring a clearance between a forehead of the Luer connector 62 and the top face 134 of the plunger 128, the arrangement being such that at the sampling/injecting position said Luer connector is in flow communication with the inlet port of the housing.

16. A blood sampling/injecting valve according to claim 15, wherein the projections are configured as bulges or protuberances formed integrally with the top face.

17. A blood sampling/injecting valve according to claim 1, wherein the plunger and the cavity are configured and dimensioned in such a manner that essentially no liquid is left in the cavity after the plunger is brought in the flow position.

* * * * *